(12) United States Patent
Fontana et al.

(10) Patent No.: US 10,722,574 B2
(45) Date of Patent: Jul. 28, 2020

(54) USE AND PREPARATION OF GLYCOLIPIDS AS ADJUVANTS IN VACCINES

(71) Applicant: CONSIGLIO NAZIONALE DELLE RICERCHE, Rome (IT)

(72) Inventors: Angelo Fontana, Avellino (IT); Emiliano Manzo, Naples (IT); Adele Cutignano, Cava de'Tirreni (IT); Raffaele De Palma, Pratola Serra (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 16/007,685

(22) Filed: Jun. 13, 2018

(65) Prior Publication Data
US 2018/0344843 A1   Dec. 6, 2018

Related U.S. Application Data

(63) Continuation of application No. 14/896,789, filed as application No. PCT/IB2014/062098 on Jun. 10, 2014, now abandoned.

(30) Foreign Application Priority Data

Jun. 10, 2013   (IT) .............................. MI2013A0949

(51) Int. Cl.
*A61K 39/39*   (2006.01)
*C07H 13/06*   (2006.01)

(52) U.S. Cl.
CPC ............. *A61K 39/39* (2013.01); *C07H 13/06* (2013.01)

(58) Field of Classification Search
CPC ............................... A61K 39/39; C07H 13/06
USPC ........................................... 514/25; 536/18.2
See application file for complete search history.

(56) References Cited

U.S. PATENT DOCUMENTS

2010/0316657 A1* 12/2010 Sprott .................. A61K 9/1272
424/184.1

OTHER PUBLICATIONS

Matsumoto et al, Colloids and Surfaces B: Biointerfaces, 2005, 46, 175-181.*

* cited by examiner

*Primary Examiner* — Ganapathy Krishnan
(74) *Attorney, Agent, or Firm* — King & Schickli, PLLC

(57) ABSTRACT

The present invention relates to beta-glycolipid derivatives, their preparation and use as adjuvants in vaccines, as being suitable for being co-administered with antigens for vaccine prophylaxis and therapy. In certain embodiments, the beta-glycolipid derivatives of the invention also in their salified or complex form, are suitable for being co-administered with antigens for both therapeutic and prophylactic purposes or for vaccine prophylaxis and therapy.

16 Claims, 7 Drawing Sheets

USE AND PREPARATION OF GLYCOLIPIDS AS ADJUVANTS IN VACCINES

This application is a continuation patent application claiming priority from U.S. patent application Ser. No. 14/896,789 filed on Dec. 8, 2015 which is the national stage of international patent application no. PCT/IB2014/062098 filed on Jun. 10, 2014 which in turn claims priority from Italian Patent Application No. MI2013A000949 filed on Jun. 10, 2013, the disclosures of which are incorporated herein by reference in their entirety.

TECHNICAL FIELD

The present invention relates to beta-glycolipid derivatives, the preparation and use thereof as adjuvants in vaccines.

The present invention originates in the pharmaceutical field and in particular in the field of adjuvants for vaccines.

Specifically, the present invention relates to beta-glycolipid derivatives and the use thereof as vaccine adjuvants, as suitable for being co-administered with antigens in vaccine for bacterial and viral diseases.

BACKGROUND

Adjuvants are substances which, when administered along with an antigen, enhance the immune response of the organism. The adjuvants used in vaccine formulations aim at triggering the immune response by administering the smallest amount of antigen possible and, therefore, avoiding any possible risks deriving from an exposure to massive doses of antigen. The vaccine procedure, performed in this manner, promotes the formation of an immune memory capable of priming a "secondary response" for its specificity and memory, and allows the organism to recognise a foreign antigen with lower efficiency and rapidity in the course of repeated exposures. The secondary response, based on the presence of pre-formed antibodies and on a greater frequency of cells specific to a given antigen, allows the quick elimination of the pathogen (from which the antigen is derived) and prevents the physio-pathological processes on which the diseases induced by the pathogen itself are based. As such, adjuvants are indispensable components in the formulation of vaccines, and have in fact been the necessary requirement for the formulation of modern vaccine formulations. For example, they are present in the formulations of vaccines against hepatitis A and B, human papilloma virus (HPV), against B-type *Haemophilus influenzae*, against pneumococcal infections and many others.

Adjuvants, despite increasing the duration and intensity of immune response, cause neither specific nor long-lasting effects on the immune system. Furthermore, they may also be used for other purposes, such as the reduction of toxicity or improvement of stability of multiple component vaccines. For these reasons, the selection of the adjuvant is often crucial for the use of modern vaccines which often contain natural or synthetic antigen substances so as to avoid the problems induced by the use of attenuated or inactivated pathogens.

Currently, the adjuvants of human vaccines more commonly used are aluminium salts, typically aluminium hydroxide, aluminium phosphate and potassium and aluminium sulphate.

More recently, the principles of innate immunity have been used to develop new classes of adjuvants which comprise various types of oil emulsions or liposomes, bacterial products such as lipid A, viral products and saponins.

For many of these substances, although the exact mechanism of action is not known, there are evidence suggesting that they act through recruitment and activation effects of cells of the innate immune system, improving the capability of processing and presenting antigens by cells specifically aimed at triggering the specific immune response, or even specific targeting mechanisms or storage effects. Recently, a great impulse to the identification and development of new adjuvants has been determined by the need of reducing toxicity in vaccines containing highly purified antigens and vaccines against chronic diseases, such as for example HIV, parasitary disease, and certain tumour forms.

Alpha-sulphoquinovosides are known which are present in all photosynthetic organisms, such as algae and terrestrial plants. (H. DANIEL, et al. 1961. *The plant sulfolipid. Identification of 6-sulfo quinovose*, JACS, 83, 1765-1766; M. LEPAGEH, et al. 1961. *The Plant Sulfolipid. Isolation and Properties of Sulfoglycosyl Glycerol*, JACS, 83, 157-159; M. MIYANO, et al. 1962.*The Plant Sulfolipid. VI. Configuration of the Glycerol Moiety*, JACS, 84, 57-58; L. Y. Okaya, 1964. *The plant sulfolipid: a crystallographic study*. Acta Cryst. 17, 1276-1282; Frank D. et al., *The Lipid Handbook* 3rd Edition, CRC Press, Boca Raton, 2007, pp. 123-128).

Currently, therefore there is a strong need of physiologically acceptable substances which find application as vaccine adjuvants.

It is an object of the present invention to find substances which are suitable as pharmaceutically acceptable adjuvants in vaccine formulations.

SUMMARY

Said object is achieved by a beta-glycolipid derivative having formula (I):

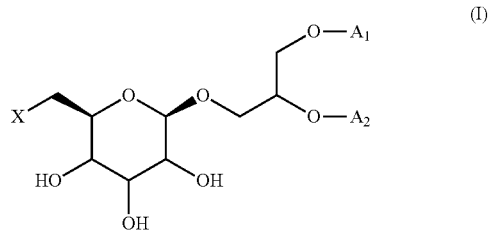

a salt or a metal complex thereof,
wherein
the acetalic bond of the anomeric carbon has ß (beta) configuration,
$A_1$ and $A_2$ are, independently of each other, saturated or monounsaturated linear or branched $C_1$-$C_{30}$ alkyl, or are an acyl —(CO)$R_1$ and —(CO)$R_2$ respectively where $R_1$ and $R_2$ are, independently of each other, saturated or monounsaturated linear or branched $C_1$-$C_{29}$ alkyl, and X is a sulphonic (—SO$_3$H), sulphuric (—OSO$_3$H), phosphoric (—OPO$_3$H$_2$), or phosphonic (—PO$_3$H$_2$) group,
for use as a vaccine adjuvant.

In another aspect, the present invention relates to a product containing at least one beta-glycolipid derivative of formula (I) and a vaccine as combined preparation for simultaneous, separate or sequential use to prevent or treat bacterial and/or viral infections.

In a further aspect, the present invention provides a product containing at least one beta-glycolipid derivative of formula (I) for use in the treatment of pathological stages connected to an alteration of immune response.

In another aspect, the present invention provides a beta-glycolipid derivative of formula (I) for use in the immunization of an animal, optionally in co-administration with an antigen against which the animal has to be immunized.

BRIEF DESCRIPTION OF THE DRAWINGS

The characteristics and advantages of the present invention will be clear from the following detailed description, from working examples provided for illustrative and non-limiting purposes, and from the appended FIGS., wherein:

FIGS. 6A-6F show the effect on the production of interleukin 12 (IL12) from dendritic cells stimulated with: FIG. 6A=mixture of natural glycolipids containing alpha-sulphoquinovosides and galactolipids purified from microalgae; FIG. 6B=mixture of sodium Salts of beta-glycolipids of formula (I); FIG. 6C=1:1 mixture of sodium salts of alpha-sulphoquinovosyl-distearoyl glycerol and alpha-sulphoquinovosyl-dipalmitoyl glycerol; FIG. 6D=mixture of sodium salts of beta-sulphoquinovosides of formula (I); FIG. 6E=1:1 mixture of sodium salts of beta-sulphoquinovosyl distearoyl-glycerol and beta-sulphoquinovosyl dipalmitoyl-glycerol; FIG. 6F=sodium salt of pure beta-sulphoquinovosyl dipalmitoyl-glycerol.

DETAILED DESCRIPTION

Figure 1:
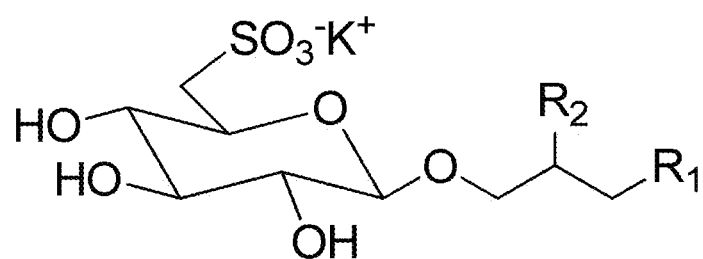
FIG. 1 shows the structure of some beta-glycolipid derivatives of formula (I), obtained by chemical synthesis and assayed on systems in vitro and in vivo.
Figure 1:
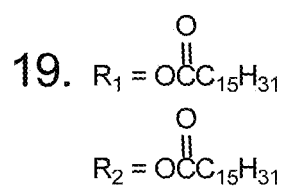
Figure 1:
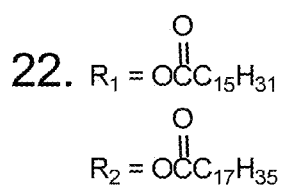
Figure 1:
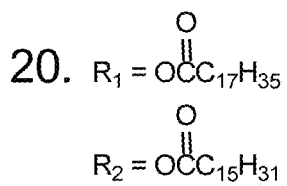
Figure 1:
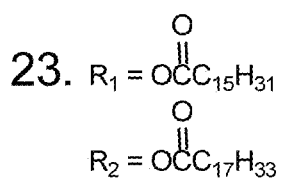
Figure 1:
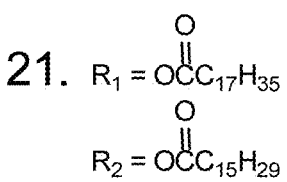
Figure 1:
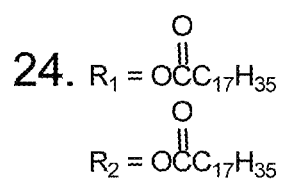

Therefore the object of the present invention is a beta-glycolipid derivative having formula (I):

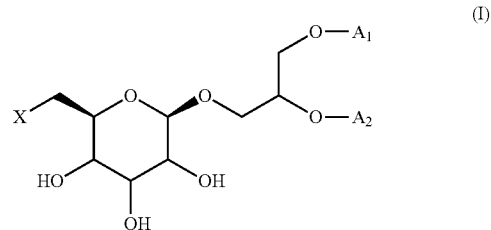

a salt or a metal complex thereof, wherein the acetalic bond of the anomeric carbon has β(beta) configuration, $A_1$ and $A_2$ are, independently of each other, saturated or monounsaturated linear or branched $C_1$-$C_{30}$ alkyl, or are an acyl —(CO)$R_1$ and —(CO)$R_2$ respectively where $R_1$ and $R_2$ are, independently of each other, saturated or monounsaturated linear or branched $C_1$-$C_{29}$ alkyl, and X is a sulphonic (—SO$_3$H), sulphuric (—OSO$_3$H), phosphoric (—OPO$_3$H$_2$), or phosphonic (—PO$_3$H$_2$) group, for use as a vaccine adjuvant.

The carbohydrate part derives from an aldohexose, or a synthetic structural analogue, with a beta configuration of the anomeric carbon.

In fact, it has surprisingly been found that these compounds enhance and/or modulate the immune response following the administration of an antigen to the organism.

The beta-sulphoquinovosides among the compounds of formula (I) are only obtainable by chemical synthesis, since in nature there are only alpha-sulphoquinovosides which have an alpha configuration of the anomeric carbon of the sugar and the extraction processes at present do not allow isolating them as pure compounds, but only as mixtures.

Preferably, $A_1$ and $A_2$ or $R_1$ and $R_2$ are independently of each other saturated or monounsaturated linear $C_6$-$C_{24}$ alkyl; for example $A_1$ and $A_2$ or $R_1$ and $R_2$ are independently of each other moieties of lauric acid, myristic acid, palmitic acid, stearic acid, arachidic acid, behenic acid or lignoceric acid.

More preferably, $A_1$ and $A_2$ or $R_1$ and $R_2$ are independently of each other saturated or monounsaturated linear $C_{14}$-$C_{18}$ alkyl.

In preferred embodiments, A1 and A2 are an acyl —(CO)R1 and an acyl —(CO)R2 respectively, where $R_1$ and $R_2$ are independently of each other a moiety of pentadecanoic acid, palmitic acid, heptadecanoic acid, or stearic acid.

In other embodiments, the beta-glycolipid derivative of formula (I) is in the form of a salt thereof, wherein X is a —$SO_3^-$, —$OSO_3^-$, —$OPO_3^{2-}$, —$PO_3^{2-}$, alkali or alkaline-earth metal group.

In particularly preferred embodiments, in the beta-glycolipid derivative of formula (I), X is —$SO_3H$, —$SO_3Na$, or —$SO_3K$.

In further embodiments, the beta-glycolipid derivative of formula (I) is in the form of a complex thereof with aluminium.

In some aspects, the invention provides a vaccine adjuvant comprising at least one beta-glycolipid derivative of formula (I), a pharmaceutically acceptable salt or complex thereof. Examples of pharmaceutically acceptable salt of the beta-glycolipid derivative of formula (I) comprise salts of a monovalent cation such as sodium or potassium.

Particularly preferred compounds of formula (I) are:
sodium or potassium salt of 1,2-diacyl-3-[1'β-(6-sulpho)-quinovosyl]-glycerol,
1,2-distearoyl-3-[1'β-(6-sulpho)-quinovosyl]-glycerol,
1,2-dipalmitoyl-3-[1'β-(6-sulpho)-quinovosyl]-glycerol,
1-palmitoyl-2-stearoyl-3-[1'β-(6-sulpho)-quinovosyl]-glycerol, and
1-stearoyl-2-palmitoyl-3-[1'β-(6-sulpho)-quinovosyl]-glycerol.

In accordance with another aspect, the present invention relates to a beta-glycolipid derivative of formula (I) and an antigen or vaccine as combined preparation for simultaneous, separate or sequential use to prevent or treat infectious diseases.

Typically, the compounds of the invention find application in preventing and/or treating infectious diseases of the bacterial, viral or mixed type.

In another aspect, the present invention relates to the use of the beta-glycolipid derivative of formula (I) as vaccine adjuvant.

In accordance with a further aspect, the present invention provides a beta-glycolipid derivative of formula (I) for use in the treatment or prevention of pathological stages connected to an alteration of immune response.

In accordance with a further aspect, the present invention provides a beta-glycolipid derivative of formula (I) for use in the immunization of an mammal, optionally in co-administration with an antigen against which the mammal has to be immunized.

The compounds of the invention, or the pharmaceutical compositions comprising the same, find application in particular in the treatment of humans.

It was further found that the beta-glycolipid derivative of formula (I) stimulates the production of specific groups of cytokines by the circulating monocytes of peripheral blood. In particular, the beta-glycolipid derivative of formula (I) is capable of increasing the production of interleukins (for example, IL-12) ans sustaining a specific immune response.

Figure 3A:
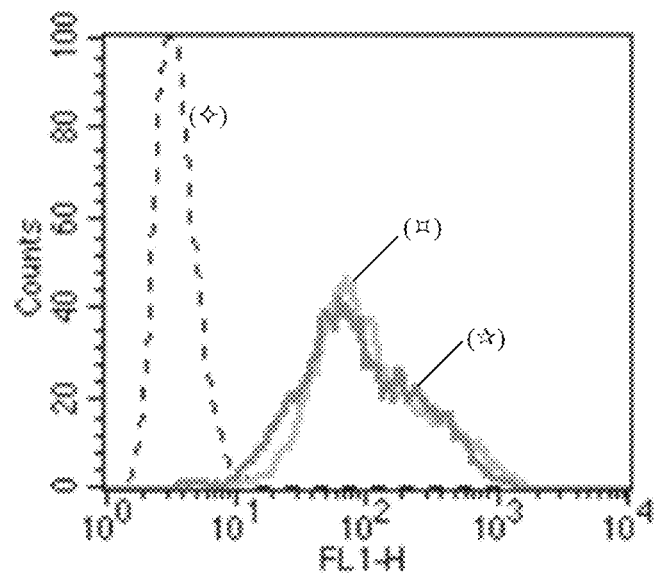
FIGS. 3A and 3B show a comparison in the expression in human dendritic cells of Class II HLA molecule co-stimulated with TNF and by a mixture of alpha-sulphoquinovosides synthesized on the model of natural compounds present in photosynthetic organisms (FIG. 3A) and by a mixture of synthetic beta-sulphoquinovosides having general formula (I) (FIG. 3B). The Class II HLA expression characterises the maturation of these cells and makes them capable of triggering the immune response in an effective manner. The results show that natural alpha-sulphoquinovosides are ineffective in stimulating dendritic cells, while beta-sulphoquinovosides determine a deep variation in the degree of maturation. The same result is achieved with the co-stimulation with lipopolysaccharide instead of TNF or with the stimulation with the two classes of sulpholipids; (✧) Control; (¤) Human dendritic cells stimulated with TNF; (☆) Human dendritic cells co-stimulated with TNF and alpha-sulphoquinovoside; (★) Human dendritic cells co-stimulated with TNF and beta-sulphoquinovoside.
Figure 3B:
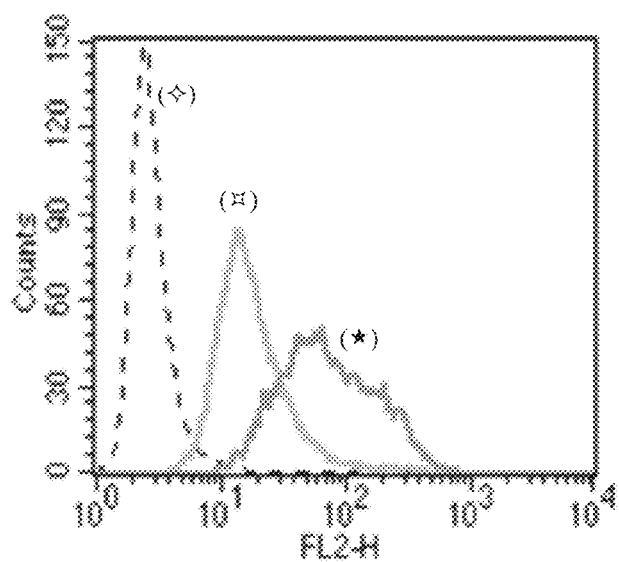
Figure 4:
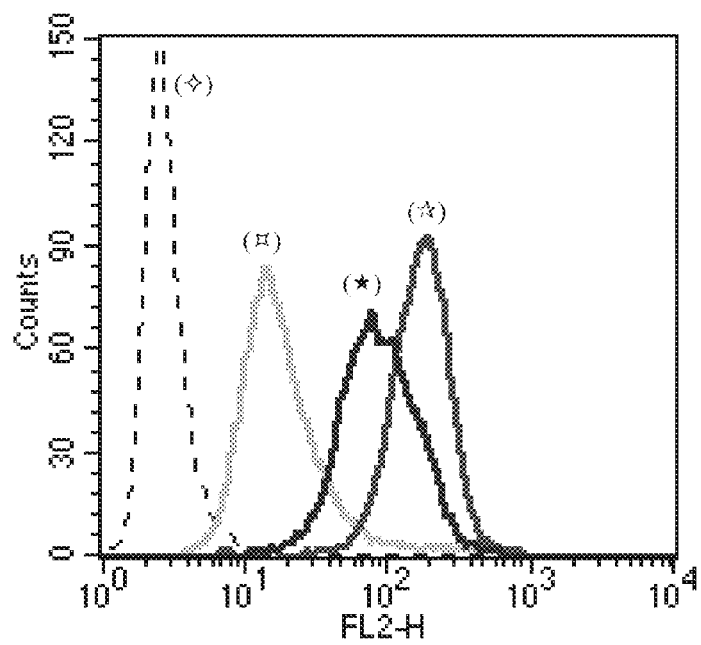
FIG. 4 shows the interference of beta-sulphoquinovosides (in particular of the preferred compound beta-sulphoquinovosyl dipalmitoyl-glycerol) in the expression in human dendritic cells of Class II HLA molecule stimulated by TNF and lipopolysaccharide (LPS) (positive control). The response shows the absence of interaction between the different classes of molecules; (✧) Human dendritic cells control; (¤) Human dendritic cells co-stimulated with TNF; (☆) Human dendritic cells co-stimulated with lipopolysaccharide; (★) Human dendritic cells co-stimulated with TNF and lipopolysaccharide and beta-sulphoquinovosyl-di-palmitoyl-glycerol.
Figure 5:
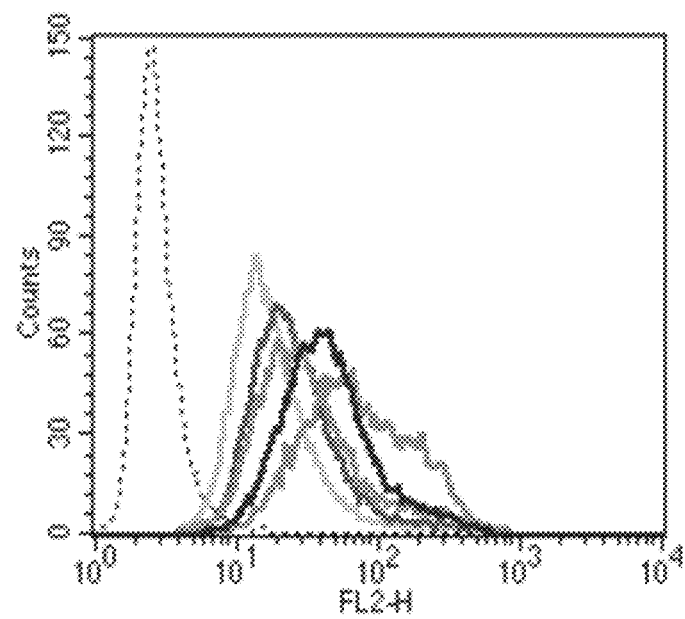
FIG. 5 shows the dose-dependent effect of the preferred compound beta-sulphoquinovosyl dipalmitoyl-glycerol, on dendritic cells obtained from peripheral blood of normal donors; Dashed curve: Human dendritic cells control; Solid curves: human dendritic cells stimulated with increasing concentrations from 10ng/ml to 100μg/ml beta-sulphoquinovosyl-di-palmitoyl-glycerol.
Figure 6A:
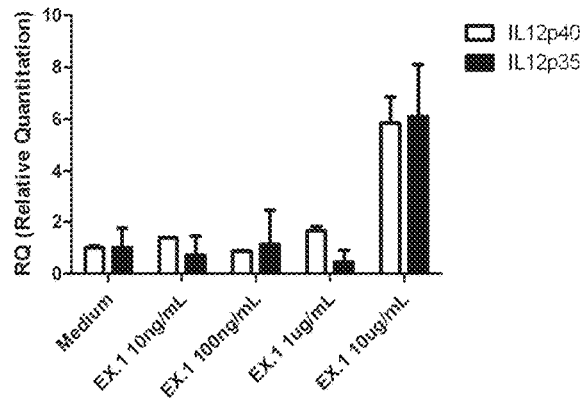
Figure 6B:
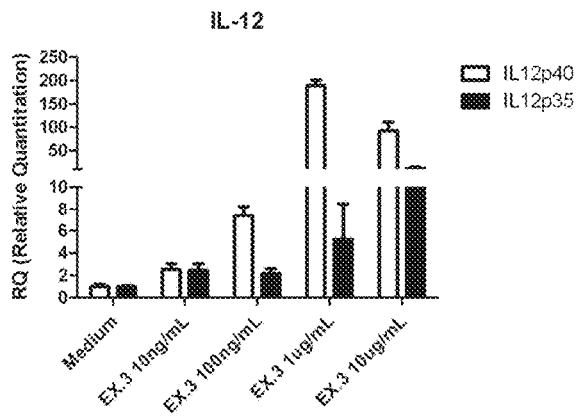
Figure 6C:
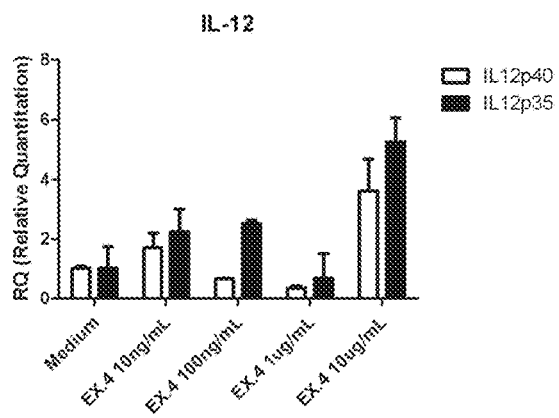
Figure 6D:
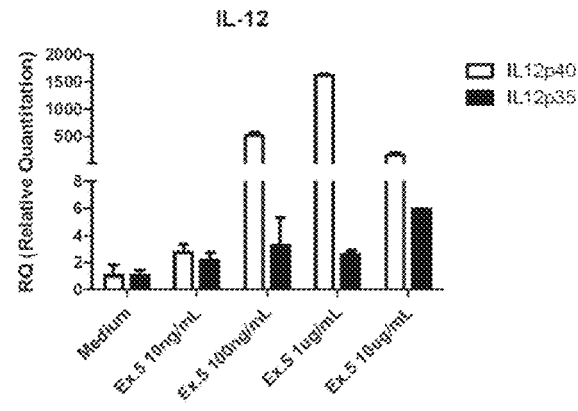
Figure 6E:
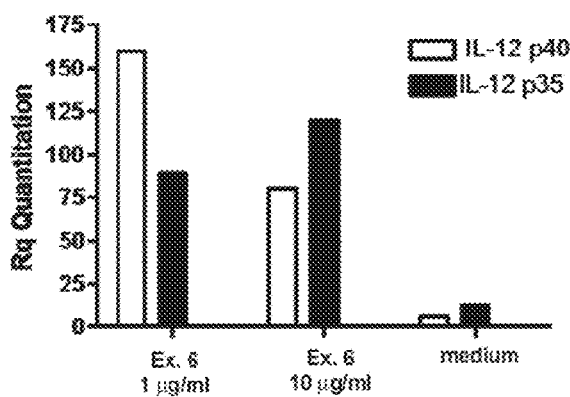
Figure 6F:
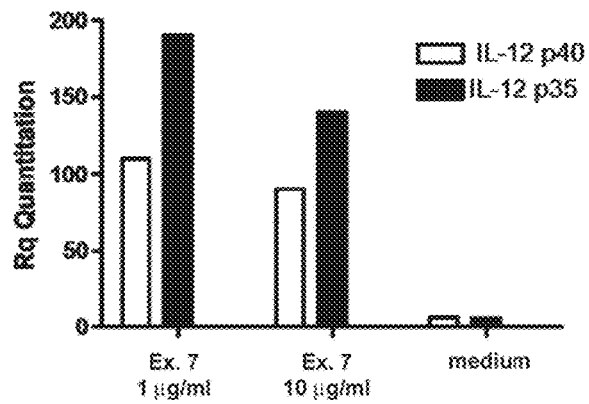

As will become clear from the following Examples, differently from the beta-glycolipid derivative of formula (I), natural glycolipids with an alpha configuration of anomeric carbon of sugar, including natural alpha-sulphoquinovosides obtained from algae and terrestrial plants, do not have any adjuvant activity (FIGS. 3A and 3B).

In accordance with this aspect, the present invention further provides a method for increasing the production of immunoglobulins and lymphokines, and sustaining a specific immune response administering to an organism an effective amount of at least one beta-glycolipid derivative of formula (I).

In a further aspect, the invention provides a pharmaceutical composition comprising at least one beta-glycolipid derivative of formula (I) for use in the treatment or prevention of bacterial or viral infections.

The pharmaceutical composition of the present invention includes any composition produced by mixing a beta-glycolipid derivative of formula (I) of the present invention and a pharmaceutically acceptable carrier. Such a composition is suitable for pharmaceutical use in an animal or in humans. The pharmaceutical compositions of the present invention include a therapeutically effective amount of one or more beta-glycolipid derivatives of formula (I), or a pharmaceutically acceptable salt thereof, and a pharmaceutically acceptable carrier.

The compositions may conveniently be presented in a single-dose form and prepared by any of the methods known in the pharmaceutical art.

A pharmaceutical composition may optionally contain other active ingredients, typically one or more vaccines.

The term 'carrier' includes any excipient or diluent, with which a glycolipid of the invention is administered.

Any carrier or excipient suitable for the desired preparation for administration is contemplated for use with the beta-glycolipid derivative of formula (I) described above. The carrier may take a wide variety of forms depending on the form of preparation desired for administration, for example, oral or parenteral (including intravenous administration).

In the preparation of the compositions for the form of oral dosage, it is possible to use any usual pharmaceutical means, such as, for example, water, glycols, oils, alcohols, flavouring agents, preservatives, colouring agents and the like in the case of liquid oral preparations, such as, for example, suspensions, elixirs and solutions; or carriers, such as starches, sugars, microcrystalline cellulose, diluents, granulating agents, lubricating agents, binding agents, disaggregating agents and the like in the case of solid oral preparations, such as, for example, powders, hard and soft capsules and tablets, with the solid oral preparations being preferred with respect to the liquid preparations.

In some embodiments, the beta-glycolipid derivative of formula (I) of the present invention may be used with another compound having the same or different activity to prepare a pharmaceutical composition.

In certain embodiments, the beta-glycolipid derivative of formula (I) of the present invention may be combined with a vaccine in a mixture with a suitable pharmaceutical carrier and/or excipient in accordance with the conventional manufacturing techniques of pharmaceutical compounds.

The compositions include compositions suitable for parenteral administration including subcutaneous, intramuscular and intravenous administration, lung, nasal, rectal, topical or oral administration.

An exemplary route of administration is the parenteral route. For example, the beta-glycolipid derivative of formula (I), or a pharmaceutical composition containing the same as an active ingredient, may be administrated intramuscularly, intravenously, intracutaneously or subcutaneously. A pharmaceutical composition or preparation to be administered parenterally may be formulated by dissolving, suspending or emulsifying at least one beta-glycolipid derivative of formula (I), in a suitable aqueous or oil-based solvent, such as for example a vegetable oil, a glyceride with a fatty acid, an ester of a higher fatty acid using commonly used pharmaceutical techniques. The pharmaceutical composition or preparation for parenteral use may contain at least one excipient or carrier, such as, for example, a solubilizing agent, a suspending agent, an emulsifying agent, a stabilizing agent and a preservative.

In certain embodiments, such compositions and preparations may contain at least 0.1% of at least one beta-glycolipid derivative of formula (I). The proportion of glycolipid in these compositions may, of course, be varied and may conveniently be of about 1% to about 60% by unit weight. The amount of beta-glycolipid derivative of formula (I) in such prophylactically or therapeutically useful compositions is such that a therapeutically or prophylactically effective dosage will be achieved.

The administration of the compositions is carried out by following a protocol and a dosage sufficient to determine or increase the immune response in the treated subject. In certain embodiments, in the pharmaceutical compositions of the present invention the beta-glycolip derivative of formula (I) is generally formulated in dosage units. The dosage unit may contain from 0.1 to 1000 mg of a beta-glycolipid derivative of formula (I) and per dosage unit for daily administration. In some embodiments, the effective amounts for the formulation will depend on the seriousness of the disease, disorder or condition, on previous therapy, on the health of the individual and on the response to the drug. In some embodiments, the dose is within the range of 0.001% by weight to 60% by weight of the formulation. When used in combination with one or more other active ingredients, typically vaccines, the beta-glycolipid derivative of formula (I) of the present invention and the other active ingredients may be used in smaller doses than when in each is used alone. As regards the formulations relative to any variety of route of administration, suitable methods and suitable formulations for the administration of drugs are disclosed in *Remington's Pharmaceutical Sciences*, XVII Edizione, Gennaro et al. Ed., Mack Publishing Co., 1985, and *Remington's Pharmaceutical Sciences*, Gennaro AR ed. XX Edition, 2000, Williams & Wilkins Pa., USA, and *Remington: The Science and Practice of Pharmacy*, XXI Edition, Lippincott Williams & Wilkins Ed., 2005; and in *Ansel's Pharmaceutical Dosage Forms and Drug Delivery Systems*, VIII Edition. Lippincott Williams & Wilkins Ed., 2005.

The administration dosage of the beta-glycolipid derivative of formula (I) of the invention varies depending on the form and route of administration and on the type of disease to prevent or treat.

By way of example, in the case of parenteral administration, the daily dosage of the beta-glycolipid derivative of formula (I) may be of 0.1 to 100 /kg of body weight.

Definitions

All the technical and scientific terms used herein have the same meaning as commonly understood by a person of ordinary skill in the art, unless otherwise stated.

The following terms, used in the specification and in the claims of the present application, have the meaning specified hereinafter, unless otherwise defined.

Within the scope of the present invention, the term "alkyl" means a saturated or monounsaturated hydrocarbon group, linear or branched, containing 1 to 30 carbons. In certain embodiments, alkyl refers, in particular, to chains having 6 to 24 carbons.

Examples of such group include methyl, ethyl, n-propyl, isopropyl, pentyl, eicosyl.

Any alkyl group may be non substituted or substituted with one or more substituents.

The term "acyl" denotes a functional group corresponding to a carboxylic acid freed of its —OH group.

The term "aldohexose" means a sugar having six carbons with the aldehyde function at C-1.

Within the scope of the present invention, the term "vaccines" means substances which provide support and enhancement to the immune response of a medication against an infectious disease. Such medication may contain organisms inactivated by chemical or physical means while maintaining appropriate immunogenic properties, living organisms which are usually free of any virulence or which have been treated to mitigate their virulence while maintaining suitable immunogenic properties, antigens extracted from or secreted by infectious agents, antigens produced by recombinant DNA technology, a recombinant vector producing antigens in vivo in the vaccinated host, DNA plasmid, antigens produced by in vitro synthesis.

Figure 2:
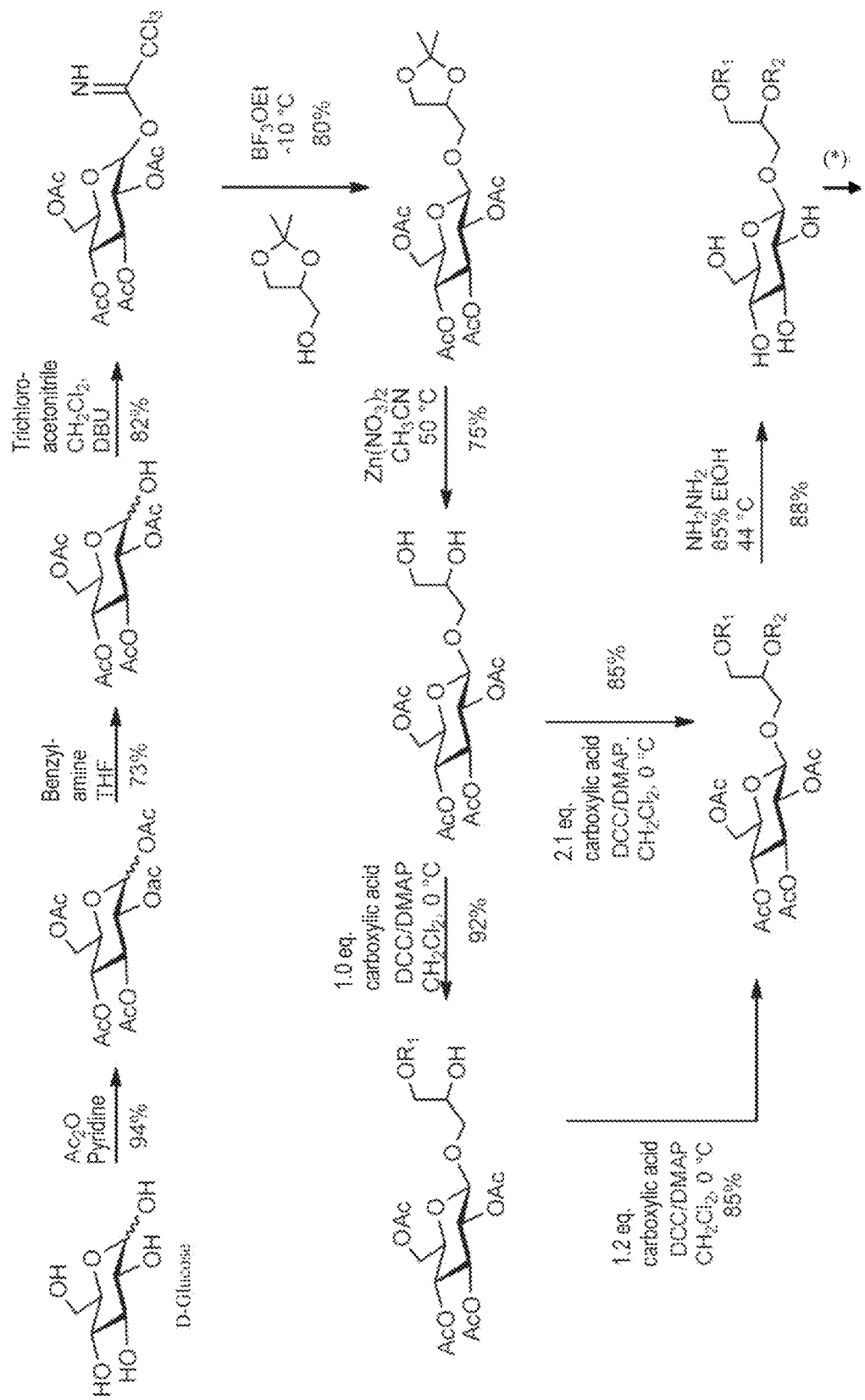
FIG. 2 shows a preferred synthesis scheme for the preparation of beta-glycolipid derivatives of formula (I), where $R_1$=acyl 1, such as palmitoyl, oleoyl, stearoyl, myristoil, capryloyl, vaccenoyl, or lauroyl, and $R_2$=acyl 2, such as palmitoyl, oleoyl, stearoyl, myristoyl, capryloil, vaccenoyl, or lauroyl.
Figure 2:
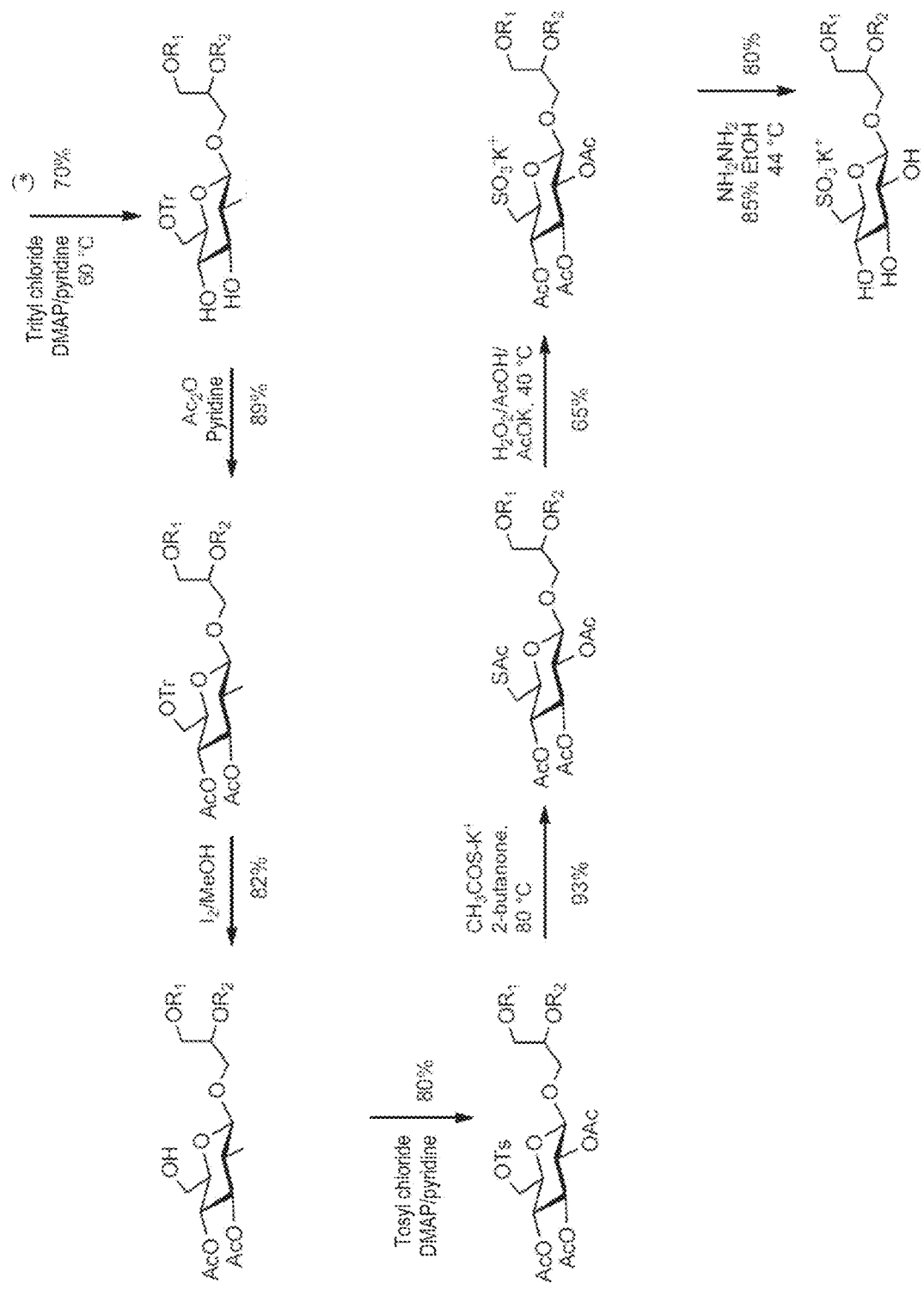

In one embodiment, the beta-glycolipid derivative of formula (I) of the invention is prepared according to the synthesis scheme described in FIG. 2 starting from per-acetylated D-glucose.

Following selective de-acetylation of the anomeric position with benzylamine, coupling with glycerol 1,2-O-isopropylidene through the methodology of trichloroacetaimidate leads to the glucolyl-isopropylidene derivative with yields near 80%. The acetate groups, in particular the one at position 2, determine the high stereo-selectivity of the reaction with the β-orientation of the newly formed glycosidic bond, as shown by the value of H-1'($\delta$=4.51, J=7.8 Hz) in the $^1$H-NMR spectrum.

Following selective hydrolysis of the isopropylidene moiety by zinc nitrate hexahydrate in acetonitrile, the condensation with one or two equivalents of organic acids (for example, stearic or palmitic acid) alternatively produces the mono- or di-acyl derivatives. In this way, the method allows a stepwise introduction of different substituents at the glycerol positions. Since primary hydroxyl is widely promoted in the coupling reaction with an equimolar amount of reactant, the introduction sequence allows controlling the type of substitution at positions sn-1 and sn-2 (sn=nucleophilic substitution) of glycerol, thus establishing the regiospecificity of the substitution on synthetic glycoglycerol.

The selective removal of the acetyl groups on glucopyranose with hydrazine monohydrate produces the beta-glucosyl-diacylglycerols. In particular, using 2.4 mole hydrazine per acetyl and a temperature below 45° C., the reaction leads to the beta-glucosyl-diacetylglycerols with yields higher than 88%.

Following tritylation on the primary alcohol of sugar (compounds 13-15, 70%), and acetylation of secondary functions (89%), the introduction of two orthogonal protecting groups on hydroxyl groups is obtained. The removal of trityl (82%), followed by activation of the primary hydroxyl function by tosylation (80%), allows introducing the sulphur-carbon bond through the formation with high yields (93%) of a thioacetate. The thioester function of this latter compound is easily oxidized to the corresponding sulphonate (65%) which, by selective hydrolysis with hydrazine, leads to the beta-sulphoquinovosyl diacylglycerols, among with the preferred compound beta-sulphoquinovosyl-di-palmitoylglycerol (86%). The possibility of introducing different organic acids on glycerol allows the application of this synthetic scheme to all the beta-glycolipid derivatives of formula (I). Furthermore, the synthetic sequence of FIG. 2 also allows preparing derivatives of various aldohexoses (for example, allose, altrose, mannose, gulose and galactose), substituted in position 6 with phosphate ($H_2PO_4$), phosphonate ($H_2PO_3$), sulphate ($HSO_4$), sulphonate ($HSO_3$) groups. Starting from 1,2-O-isopropylidene having known chirality, the synthetic scheme of FIG. 2 also allows the synthesis of enantiomerically pure sulpho- or phospho-glycosyl-1,2-diacyl-glycerols.

It should be understood that also all the possible combinations of the preferred aspects of the process as reported hereinabove are similarly described.

As illustrated in FIGS. 3A, 3B, 4, 5, 6A-6F and 7, the beta-glycolipid derivatives of formula (I), in pure form or in mixture, are capable of acting on the immune system triggering the cell response in vitro and in vivo by activating specialized cell lines, generally known as antigen-presenting cells (APC).

In particular, the process involves dendritic cells which, presenting the antigens for virgin T lymphocytes, trigger the immune response de novo. Dendritic cells may essentially exist in an "off" (immature cells) and "on" state (mature cells). Maturation implies the increase in production of trigger molecule levels, like specific cytokines, capable of adjusting T cell response, and transforms the cells so that they may internalize exogenous antigens and process them for the later presentation mediated by class II MHC molecules.

In accordance with these mechanisms, the beta-glycolipid derivatives of formula (I), in a mixture or in a pure form, such as for example beta-sulphoquinovosyl-di-palmitoyl-glycerol, are capable of causing the maturation of dendritic cells, as shown by the increase in expression of class II MHC molecules (FIGS. 3A, 3B, 4 and 5) and by the increase in production of cytokines, such as for example Interleukin 12 (FIGS. 6A-6F).

On the contrary, as seen in particular in FIGS. 3A and 3B, natural compounds with alpha configuration of the anomeric carbon of sugar, including the natural alpha-sulphoquinovosides obtained by algae and terrestrial plants, do not possess any capability of stimulating dendritic cells.

The maturation induced by the beta-derivatives of the present invention leads to an increase in immunization and to a reduction in the capability of capturing and processing the antigen.

Figure 7:
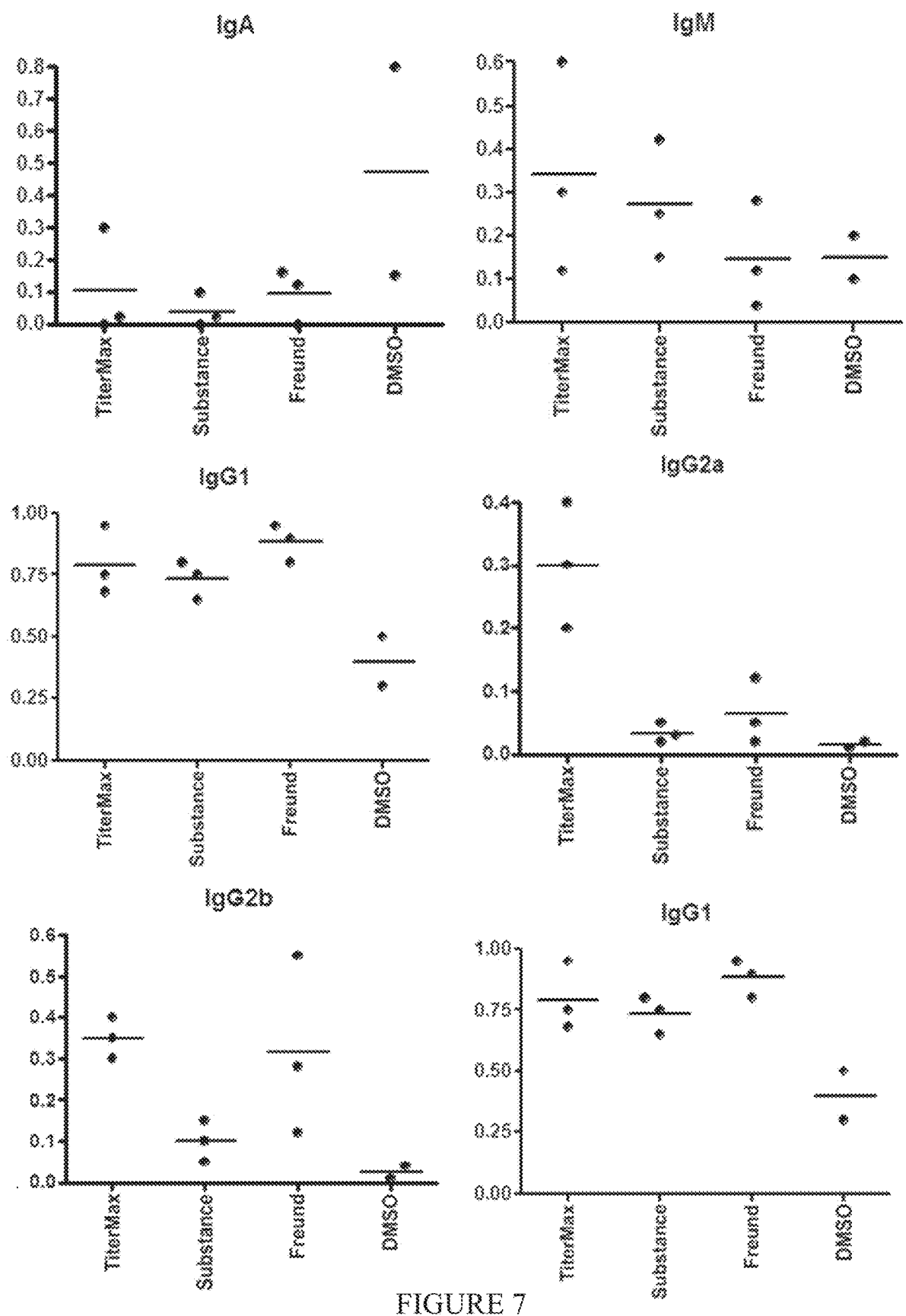
FIG. 7 shows the values of the specific antibody titer after in vivo immunization of mice injected with Ovalbumin plus the preferred compound beta-sulphoquinovosyl dipalmitoyl-glycerol (Substance). The experiment is conducted in comparison with animals immunized with Ovalbumin and two new-generation commercial-grade adjuvants. Freund (aqueous emulsion of oil drops and killed tuberle bacilli) and TiterMax (oily emulsion containing squalene). DMSO alone, used as carrier for the administration of beta-sulphoquinovosyl dipalmitoyl-glycerol, is the negative control. The specific IgG values show an adjuvant effect of the beta-sulphoquinovosyl dipalmitoyl-glycerol, comparable to that of the two adjuvants currently already used for the formulation of vaccines.

As exemplified with the preferred compound beta-sulphoquinovosyl dipalmitoyl glycerol, the beta-glycolipid derivatives of formula (I) have also been used as adjuvants to immunize with ovalbumin 4 groups of female C56 Bl/6 mice (n=5) (FIG. 7). According to the conventional immunization protocol, 50 μg of the protein are co-administered along with 0.5 mg of beta-sulphoquinovosyl dipalmitoyl glycerol in DMSO. The immunogenic capability of the product was also verified by comparing the response of mice to ovalbumin co-administered with two latest-generation adjuvants (Titermax and Freund) according to the manufacturer's instructions for Titermax and Freund. A fourth group of mice was used as control and was treated with DMSO alone. The mice were then subjected to retro-orbital bleeding at 7, 15 and 21 days and the levels of IgM, IgA, IgG1, IgG2a, IgG2b, IgG3 were measured by ELISA. The production of OVA-specific immunoglobulins, in particular of IgG1, was comparable between the two adjuvants and the betasulphoquinovosyl dipalmitoyl glycerol, demonstrating that compounds of the invention have immunogenic properties and may be used as vaccine adjuvants.

It should be understood that also all the possible combinations of the preferred aspects of the compounds of formula (I) of the invention as reported hereinabove are described and therefore similarly preferred.

It should be further understood that all the aspects identified as preferred and advantageous for the compounds of formula (I) are also to be considered equally preferred and advantageous for the preparation and use of the same.

Working examples of the present invention are provided below for illustrative purposes.

EXAMPLES

General Method for Synthesizing 1,2-O-Diacyl-3-[1'-β-Glucosyl]-Glycerols—Compounds Useful for the Synthesis of Beta-Glycolipid Derivatives of Formula (I) (See FIG. 2)

1,2-O-isopropylidene Glycerol: 2,2-dimetoxypropane (4 mL) and paratoluenesulphonic acid (300 mg) are added to glycerol (2.0 g, 0.022 mol) dissolved in N,N-dimethylformamide (4 mL). After stirring overnight at room temperature, the reaction mixture is extracted with ice and diclo-romethane and the organic phase purified on silica gel column using a gradient of petroleum ether and ethyl ether to obtain the 1,2-O-isopropylidene glycerol (2.0 g, 0.015 mol, 68%).

Peracetylated Glucose: D-glucose (1.00 g, 0.0056 mol) is dissolved in pyridine (13 mL) and acetic anhydride (5 mL). After 3 hours, the reaction mixture is extracted with chloroform and water and the organic phase purified on silica gel column using a gradient of petroleum ether and ethyl ether to obtain the peracetylated glucose (2.10 g, 0.0054 mol, 94%). $^1$H-NMR (400 MHz, $CDCl_3$): δ 6.32 (1H, d, J=3.3 Hz, H-1', α-anomer), 5.71 (1H, d, J=8.18 Hz, H-1', β-anomer), 5.46 (1H, dd, J=9.7, 9.7 Hz, H-4'), 5.12 (1H, H-2'), 5.11 (1H, H-3'), 4.29 (1H, m, H-5'), 4.26 (1H, dd, J=6.37, 11.1 Hz, H-6'a), 4.11 (1H, dd, J=6.7, 11.1 Hz, H-6'b), 2.17-2.00 (15H, —$COCH_3$); HRESIMS m/z 413.1064 [M+Na]$^+$ (413.1060 calcd. for $C_{16}H_{22}O_{11}Na$).

2,3,4,6-Tetraacetylated Glucose: 1.5 benzylamine equivalents are added to peracetylated glucose (1.00 g, 0.0026 mol) in tetrahydrofurane (10 mL). After one night at room temperature and after extraction with water and chloroform, the organic phase is purified on silica gel column using a gradient of petroleum ether and ethyl ether 0.66 g 2,3,4,6-tetraacetylated glucose is obtained (0.0019 mol, 73%). HRESIMS m/z 371.0957 [M+Na]$^+$(371.0954 calcd. for $C_{14}H_{20}O_{10}Na$).

Glucose 2,3,4,6-tetraacetyl-1-trichloroacetimidate: 2,3,4,6-tetraacetylated glucose (0.66 g, 0.0019 mol) is dissolved in 6 mL anhydrous dicloromethane. The mixture is then supplemented with 10 equivalents of trichloroacetonitrile and 0.2 equivalents of 1,8-Diazabicyclo[5.4.0]undec-7-ene (DBU). After stirring for 2 hours at 0° C. on 3 Å molecular sieves, the reaction mixture is filtered and purified on silica gel column using a gradient of petroleum ether and ethyl acetate so as to obtain 0.77 g glucose 2,3,4,6-tetraacetyl-1-trichloroacetimidate (0.0016 mol, 82%). $^1$H-NMR (400 MHz, $CDCl_3$): δ 6.56 (1H, d, J=3.8 Hz, H-1'), 5.57 (1H, dd, J=9.2, 9.2 Hz, H-3'), 5.18 (1H, dd, J=9.2, 9.2 Hz, H-4'), 5.14 (1H, dd, J=3.5, 9.2 Hz, H-2'), 4.28 (1H, m, H-6'a), 4.26 (1H, m, H-5'), 4.13 (1H, m, $H_2$-6'b), 2.09-2.01 (12H, $COCH_3$); HRESIMS m/z 514.0047 [M+Na]$^+$ (514.0050 calcd. for $C_{16}H_{20}Cl_3NO_{10}Na$).

1,2-O-isopropylidene-3-[1'β-(2',3',4',6'-tetraacetyl)-glucosyl]-glycerol: Glucose 2,3,4,6-tetraacetyl-1-trichloroacetimidate (0.74 g, 0.0015 mol) is dissolved in anhydrous dichloromethane (6 mL) and treated with 1.5 equivalents of 1,2-O-isopropylidene glycerol and boron trifluoride etherate (81 µL, 0.33 mmol) under argon at −20° C. on molecular sieves. After stirring for 2 hours, further 81 µL boron trifluoride etherate (0.33 mmol) is added and the reaction is allowed to slowly warm until reaching room temperature. After stirring overnight, the reaction mixture is neutralized with triethylamine (130 µL) and filtered on celite. The filtrate is then purified on silica gel column using a gradient of petroleum ether and ethyl etherso as to obtain 0.55 g 1,2-O-isopropylidene-3-[1'β-(2',3',4',6'-tetraacetyl)-glucosyl]-glycerol (0.0012 mol, 80%). The spectrum data are the same as those in the literature HRESIMS m/z 485.1639 [M+Na]$^+$ (485.1635 calcd. for $C_{20}H_{30}O_{12}Na$).

2',3',4',6'-tetraacetylglucosyl-(1'β→3)-glycerol: 1,2-O-isopropylidene-3-[1'β-(2',3',4',6'-tetraacetyl)-glucosyl]-glycerol (0.55 g, 0.0012 mol) and 5 equivalents of zinc nitrate hexahydrate are suspended in acetonitrile (8 mL). After 6 hrs. at 50° C., the solvent is evaporated at reduced pressure and the reaction crude is purified on silica gel column using a gradient of petroleum ether and ethyl ether. 0.38 g 2',3',4',6'-tetraacetylglucosyl-(1'β→3)-glycerol is obtained (0.0009 mol, 75%). The spectrum data of the compound are the same as those in the literature, HRESIMS m/z 445.1319 [M+Na]$^+$ (445.1322 calcd. for $C_{17}H_{26}O_{12}Na$).

1,2-diacyl-3-[1'-β-(2',3',4',6'tetraacetyl)-glucosyl]-glycerol: In anhydrous conditions, 1 equivalent of 2',3',4',6'-tetraacetylglucosyl-(1'β→3)-glycerol, 2 equivalents of dicyclohexylcarbodiimide and 0.1 equivalents of DMAP are dissolved in anhydrous dichloromethane (1 mL per 0.1 mmol glucosyl derivative). To the solution, 1.05 equivalents of fatty acid are slowly added and the reaction mixture is kept under stirring for 12 hrs. at room temperature. Once this time has elapsed, to the solution further 1.05 equivalents of fatty acid having the same structure or a structure differing from the first one are added. The mixture is kept under stirring for 24 hrs. at room temperature. After evaporation of the solvent at reduced pressure, the crude reaction mixture is purified on silica gel column using a gradient of petroleum ether and ethyl ether. The method leads to a yield above 90% of 1,2-diacyl-3-[1'-β-(2',3',4',6'tetraacetyl)-glucosyl]-glycerol.

1,2-Diacyl-3-[1'-β-glucosyl]-glycerol: 1 equivalent of 1,2-diacyl-3-[1'-(2',3',4',6'-tetraacetyl)-glucosyl]-glycerol and 1.1 equivalents of hydrazine monohydrate are dissolved in ethanol/water 85:15 (1.5 mL per 0.1 mmol glucosyl derivative). The reaction mixture is kept under stirring for 6 hrs. at 44° C. and then brought to dryness at reduced pressure. The subsequent purification on silica column with a gradient of chloroform and methanol yields the corresponding 1,2-Diacyl-3-[1'-glucosyl]-glycerol with yields close to 90%.

1,2-dipalmitoyl-3-[1'-glucosyl]-glycerol: 1,2-dipalmitoyl-3-[1'-(2',3',4',6'tetraacetyl)-glucosyl]-glycerol (0.416 g, 0.00044 mol) and hydrazine monohydrate (0.262 g, 0.0052 mol) are dissolved in 8 ml ethanol/water 85:15. The reaction mixture is kept under stirring for 6 hrs. at 44° C. and then brought to dryness at reduced pressure. The subsequent purification on silica column with a gradient of chloroform and methanol allows isolating 0.292 g 1,2-dipalmitoyl-3-[1'-glucosyl]-glycerol (0.00037 mol, 85%). The spectroscopic data of the compound are the same as those in the literature; HRESIMS m/z 753.5497 [M+Na]$^+$ (753.5493 calcd. for $C_{41}H_{78}O_{10}Na$).

1-palmitoyl-2-stearoyl-3-[1'-glucosyl]-glycerol: 1-palmitoyl-2-stearoyl-3-[1'-(2',3',4',6'-tetraacetyl)-glucosyl]-glycerol (0.402 g, 0.00043 mol) and hydrazine monohydrate (0.253 g, 0.0050 mol) are dissolved in 8 ml ethanol/water 85:15. The reaction mixture is kept under stirring for 6 hrs. at 44° C. and then brought to dryness at reduced pressure. The subsequent purification on silica column with a gradient of chloroform and methanol allowed isolating 0.283 g 1-palmitoyl-2-stearoyl-3-[1'-glucosyl]-glycerol (0.00036 mol, 86%). The spectroscopic data of the compound are the same as those in the literature; HRESIMS m/z 781.5801 [M+Na]$^+$ (781.5806 calcd. for $C_{43}H_{82}O_{10}Na$).

1,2-distearoyl-3-[1'-glucosyl]-glycerol: 1,2-distearoyl-3-[1'-(2',3',4',6'tetraacetyl)-glucosyl]-glycerol (0.438 g, 0.00046 mol) and hydrazine monohydrate (0.276 g, 0.0055 mol) are dissolved in 8 ml ethanol/water 85:15. The reaction mixture is kept under stirring for 6 hrs. at 44° C. and then brought to dryness at reduced pressure. The subsequent purification on silica column with a gradient of chloroform and methanol allowed isolating 0.318 g 1,2-distearoyl-3-[1'-glucosyl]-glycerol (0.00040 mol, 88%). The spectroscopic and spectrometric data of the compound are the same as those in the literature; HRESIMS m/z 809.6116 [M+Na]$^+$ (809.6119 calcd. for $C_{45}H_{86}O_{10}Na$).

General Method for Synthesizing 1,2-O-Diacyl-3-[1'-(6-Sulpho)-Quinovosyl]-Glycerols (see FIG. 2)

1,2-Diacyl-3-[1'-β-(6'-trityl)-glucosyl]-glycerols: 1 equivalent of 1,2-Diacyl-3-[1'-β-glucosyl]-glycerol obtained as illustrated hereinabove, 1.6 equivalents of tritylchloride and 0.4 equivalents of DMAP are dissolved in pyridine (10 ml per mmol of diacyl glucosylglycerol). The reaction mixture is kept under stirring for 3 hrs. at 60° C. and evaporated and purified on silica gel column using a gradient of chloroform and methanol. The method typically allows obtaining at least 70% molar yield of 1,2-diacyl-3-[1'-(6'-trityl)-glucosyl]-glycerol.

1,2-Diacyl-3-[1'-β-(2',3',4'-triacetyl-6'-trityl)-glucosyl]-glycerols: 1 equivalent of 1,2-diacyl-3-[1'-(6'-trityl)-glucosyl]-glycerol is reacted with acetic anhydride (about 10 ml per mmol of glucosylglycerol) in anhydrous pyridine (about 20 ml per mmol of product). After stirring for 3 hours, the reaction mixture is extracted with chloroform and water and the organic phase purified on silica gel column using a gradient of petroleum ether and ethyl ether. The method typically leads to yields above 90% of 1,2-diacyl-3-[1'-(2',3',4'-triacetyl-6'-trityl)-glucosyl]-glycerol.

1,2-Diacyl-3-[1'-β-(2',3',4'-triacetyl)-glucosyl]-glycerols: 1 equivalent of 1,2-diacyl-3-[1'-(2',3',4'-triacetyl-6'-trityl)-glucosyl]-glycerol is dissolved in a 2% solution of iodine in methanol (about 50 ml per mmole of glucosylglycerol). After continuous stirring for 48 hrs. at 60° C., the reaction mixture is purified on silica gel column using a gradient of petroleum ether and ethyl ether so as to obtain the 1,2-diacyl-3-[1'-(2',3',4'-triacetyl)-glucosyl]-glycerol with yields typically above 80%.

1,2-Diacyl-3-[1'-β-(2',3',4'-triacetyl-6'-tosyl)-glucosyl]-glycerols: 1 equivalent of 1,2-diacyl-3-[1'-(2',3',4'-triacetyl)-glucosyl]-glycerol, 1 equivalent of paratoluenesulphonyl chloride and 1 equivalent of DMAP are dissolved in anhydrous pyridine (about 30 ml per mmol of glucosylglycerol) at 0° C. and under argon. After stirring for 14 hrs., the reaction mixture is brought to dryness at reduced pressure and purified on silica using a gradient of petroleum ether and ethyl ether. The method allows obtaining 1,2-diacyl-3-[1'-(2',3',4'-triacetyl-6'-tosyl)-glucosyl]-glycerols with yields equal to or higher than 80%.

1,2-Diacyl-3-[1'-(2',3',4'-triacetyl-6'-thioacetyl)-6'-deoxy-glucosyl]-glycerols: 1 equivalent of 1,2-diacyl-3-[1'-(2',3',4'-triacetyl-6'-tosyl)-glucosyl]-glycerols and 2.5 equivalents of potassium acetate are dissolved in 2-butanone (100 ml per mmole of glucosylglycerol). The reaction mixture is kept under stirring at 80° C. for 2.5 hours and then evaporated at reduced pressure. The reaction crude is purified on silica gel column using a gradient of petroleum ether and ethyl ether so as to obtain the 1,2-diacyl-3-[1'-(2',3',4'-triacetyl-6'-thioacetyl)-6-deoxy-glucosyl]-glycerol with yields above 90%.

1,2-Diacyl-3-[1'-β-(2',3',4'-triacetyl-6-sulpho)-quinovosyl]-glycerols: 1 equivalent of 1,2-diacyl-3-[1'-(2',3',4'-triacetyl-6'-thioacetyl)-6-deoxy-glucosyl]-glycerol is dissolved in an aqueous mixture containing 5 equivalents of potassium acetate, 34% w/v hydrogen peroxide (2.5 ml per mmol of glucosylglycerol) and acetic acid (about 30 ml per mmol of glucosylglycerol). The reaction mixture is kept under stirring for 14 hrs. at 40° C. before being brought to dryness at reduced pressure and then freeze-dried. The reaction crude is then purified on silica gel column using a gradient of chloroform and methanol so as to obtain 1,2-diacyl-3-[1'β-(2',3',4'-triacetyl-6'-sulpho)-quinovosyl]-glycerols with yields above 60%.

Potassium Salt of 1,2-diacyl-3-[1'β-(6-sulpho)-quinovosyl]-glycerol: 1 equivalent of 1,2-diacyl-3-[1'β-(2',3',4'-triacetyl-6'-sulpho)-quinovosyl]-glycerol and 10 equivalents of hydrazine monohydrate are dissolved in ethanol/water 85:15 (about 10 ml per mmol of sulphoquinovosyl glycerol). The mixture is kept under reaction for 3 hrs. at 44° C. before being brought to dryness at reduced pressure. The sample is purified on silica column so as to obtain 1,2-diacyl-3-[1β'-(6-sulpho)-quinovosyl]-glycerol with yields equal to or higher than 80%.

1,2-distearoyl-3-[1'β-(6-sulpho)-quinovosyl]-glycerol: 1,2-distearoyl-3-[1'β-(2',3',4'-triacetyl-6-sulpho)-quinovosyl]-glycerol (0.044 g, 0.043 mmol), prepared according to the general scheme illustrated hereinbefore, and hydrazine monohydrate (0.017 g, 0.361 mmol) are dissolved in 4.7 mL aqueous ethanol (85%). After 3 h at 44° C., the reaction mixture is evaporated and purified on silica gel column using a gradient of chloroform and methanol so as to obtain 1,2-distearoyl-3-[1'β-(6-sulpho)-quinovosyl]-glycerol (potassium salt) (compound 24) (0.030 g, 0.034 mmol, 80%). $R_f$ (chloroform/methanol 7:3)=0.15; IR (liquid film) $v_{max}$ 3400, 2940, 2862, 1750, 1351, 1343 cm$^{-1}$; $^1$H-NMR (400 MHz, CD$_3$OD): δ 5.29 (1H, m, H-2), 4.34 and 4.32 (each for 1H, d, 7.8 Hz, H-1'), 4.19 (1H, m, H-1a), 4.11 (1H, m, H-3a), 4.09 (1H, m, H-1b), 3.79-3.75 (3H, m, H-3b, H-3', H-4'), 3.42 (1H, m, H-5'), 3.24 (1H, m, H-2'), 3.18 (1H, m, H-6'a), 2.98 (1H, m, H-6'b), 2.43-2.35 (4H, m, a methylenes of the alkyl chain), 1.69-1.58 (4H, m, β methylenes of the alkyl chain), 1.43-1.29 (protons of the alkyl chain), 0.94 (6H, 2 CH$_3$); HRESIMS m/z 911.5300 [M+Na]$^+$ (911.5297 calcd. for C$_{45}$H$_{85}$NaO$_{12}$KS).

1,2-dipalmitoyl-3-[1'β-(6-sulpho)-quinovosyl]-glycerol: 1,2-dipalmitoyl-3-[1'β-(2',3',4'-triacetyl-6-sulpho)-quinovosyl]-glycerol (0.022 g, 0.022 mmol), prepared according to the general scheme illustrated hereinbefore, and hydrazine monohydrate (0.008 g, 0.180 mmol) are dissolved in 2.3 mL aqueous ethanol (85%). After 3 hrs. at 44° C., the reaction mixture is evaporated and purified on silica gel column using a gradient of chloroform and methanol so as to obtain 1,2-dipalmitoyl-3-[1'β-(6-sulpho)-quinovosyl]-glycerol (potassium salt) (0.014 g, 0.016 mmol, 74%) (compound 19); $R_f$ (chloroform/methanol 7:3)=0.15; IR (liquid film) $v_{max}$ 3400, 2940, 2862, 1750, 1351, 1343 cm$^{-1}$; $^1$H-NMR (400 MHz, CD$_3$OD): δ 5.29 (1H, m, H-2), 4.34 and 4.32 (each for 1H, d, 7.8 Hz, H-1'), 4.19 (1H, m, H-1a), 4.11 (1H, m, H-3a), 4.09 (1H, m, H-1b), 3.79-3.75 (3H, m, H-3b, H-3', H-4'), 3.42 (1H, m, H-5'), 3.24 (1H, m, H-2'), 3.18 (1H, m, H-6'a), 2.98 (1H, m, H-6'b), 2.43-2.35 (4H, m, a methylenes of the alkyl chain), 1.69-1.58 (4H, m, βmethylenes of the alkyl chain), 1.43-1.29 (protons of the alkyl chain), 0.94 (6H, 2 CH$_3$); HRESIMS m/z 855.4675 [M+Na]$^+$ (855.4671 calcd. for C$_{41}$H$_{77}$NaO$_{12}$KS).

1-palmitoyl-2-stearoyl-3-[1'β-(6-sulpho)-quinovosyl]-glycerol: 1-palmitoyl-2-stearoyl-3-[1'β-(2',3',4'-triacetyl-6-sulpho)-quinovosyl]-glycerol (0.035 g, 0.034 mmol), prepared according to the general scheme illustrated hereinbefore, and hydrazine monohydrate (0.014 g, 0.289 mmol) are dissolved in 4.7 mL aqueous ethanol (85%) (4.7 mL). After 3 h at 44° C., the reaction mixture is evaporated and purified on silica gel column using a gradient of chloroform and methanol so as to obtain 1-palmitoyl-2-stearoyl-3-[1'β-(6-sulpho)-quinovosyl]-glycerol (potassium salt) (0.021 g, 0.024 mmol, 70%). $R_f$ (chloroform/methanol 7:3) =0.15; IR (liquid film) $v_{max}$3400, 2940, 2862, 1750, 1351, 1343 cm$^{-1}$; $^1$H-NMR (400 MHz, CD$_3$OD): δ 5.29 (1H, m,H-2), 4.34 and 4.32 (each for 1H, d, 7.8 Hz, H-1'), 4.19 (1H, m, H-1a), 4.11 (1H, m, H-3a), 4.09 (1H, m, H-1b), 3.79-3.75 (3H, m, H-3b, H-3', H-4'), 3.42 (1H, m, H-5'), 3.24 (1H, m, H-2'), 3.18 (1H, m, H-6'a), 2.98 (1H, m, H-6'b), 2.43-2.35 (4H, m, α methylenes of the alkyl chain), 1.69-1.58 (4H, m, β methylenes of the alkyl chain), 1.43-1.29 (protons of the alkyl chain), 0.94 (6H, 2 CH$_3$); HRESIMS m/z 883.4986 [M+Na]$^+$ (883.4984 calcd. for C$_{43}$H$_{81}$NaO$_{12}$KS).

The invention claimed is:

1. A method for modulating the immune response following the administration of an antigen or a vaccine to a subject in need thereof, said method comprising the administration of a vaccine adjuvant composition, said vaccine adjuvant composition comprising at least one beta-glycolipid derivative of formula (I):

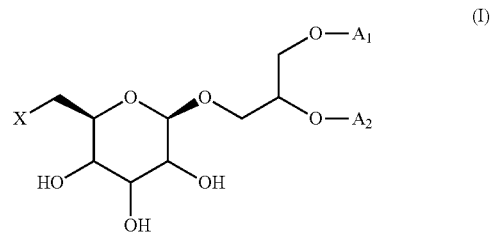

or a salt or a metal complex thereof,
wherein
the acetalic bond of the anomeric carbon has β (beta) configuration,
$A_1$ and $A_2$ are, independently of each other, saturated or monounsaturated linear or branched $C_1$-$C_{30}$ alkyl, or are an acyl —(CO)$R_1$ and —(CO)$R_2$ respectively where $R_1$ and $R_2$ are, independently of each other, saturated or monounsaturated linear or branched $C_1$-$C_{29}$ alkyl, and X is a sulphonic (—SO$_3$H), sulphuric (—OSO$_3$H), phosphoric (—OPO$_3$H$_2$), or phosphonic (—PO$_3$H$_2$) group,
wherein said at least one beta-glycolipid derivative of formula (I) stimulates the immune system by activating antigen-presenting cells.

2. The method of claim 1, wherein said antigen-presenting cells are dendritic cells.

3. The method of claim 1, wherein the vaccine adjuvant composition is co-administered with an antigen against which the subject in need thereof has to be immunized.

4. The method of claim 1, wherein, in the beta-glycolipid derivative, $A_1$ and $A_2$ or $R_1$ and $R_2$ are, independently of each other, saturated or monounsaturated linear $C_6$-$C_{24}$ alkyl.

5. The method of claim 1, wherein, in the beta-glycolipid derivative, $A_1$ and $A_2$ or $R_1$ and $R_2$ are, independently of each other, moieties of lauric acid, myristic acid, palmitic acid, stearic acid, arachidic acid, behenic acid or lignoceric acid.

6. The method of claim 1, wherein, in the beta-glycolipid derivative, $A_1$ and $A_2$ or $R_1$ and $R_2$ are, independently of each other, saturated or monounsaturated linear $C_{14}$-$C_{18}$ alkyl.

7. The method of claim 1, wherein, in the beta-glycolipid derivative, $A_1$ and $A_2$ are acyl —(CO)$R_1$ and acyl —(CO)$R_2$ respectively, where $R_1$ and $R_2$ are, independently of each other, a moiety of pentadecanoic acid, palmitic acid, heptadecanoic acid, or stearic acid.

8. The method of claim 1, wherein the beta-glycolipid derivative of formula (I) is in the form of a salt thereof, wherein X is a —SO$_3^-$, —OSO$_3^-$, —OPO$_3^{2-}$, —PO$_3^{2-}$, wherein the metal ion is from the alkali or alkaline-earth metal group.

9. The method of claim 1, wherein, in the beta-glycolipid derivative, X is —SO$_3$H, —SO$_3$Na, or —SO$_3$K.

10. The method of claim 1, wherein the beta-glycolipid derivative of formula (I) is in the form of a complex thereof with aluminium.

11. The method of claim 1, wherein said beta-glycolipid derivative is sodium or potassium salt of 1,2-diacyl-3-[1'β-(6-sulpho)-quinovosyl]-glycerol.

12. The method of claim 1, wherein said beta-glycolipid derivative is 1,2-distearoyl -3-[1'β-(6-sulpho)-quinovosyl]-glycerol.

13. The method of claim 1, wherein said beta-glycolipid derivative is 1,2-dipalmitoyl -3-[1'β-(6-sulpho)-quinovosyl]-glycerol.

14. The method of claim 1, wherein said beta-glycolipid derivative is 1-palmitoyl-2-stearoyl-3-[1'β-(6-sulpho)-quinovosyl]-glycerol or 1-stearoyl -2-palmitoyl-3-[1'β-(6-sulpho)-quinovosyl]-glycerol.

15. The method of claim 1, wherein the vaccine adjuvant composition comprises at least one beta-glycolipid derivative of formula (I), a pharmaceutically acceptable salt or metal complex thereof.

16. The method of claim 3, wherein the vaccine adjuvant composition and the antigen are provided in the form of a product or kit containing them, for their simultaneous, separate or sequential administration.

* * * * *